(12) United States Patent
Atanasoska et al.

(10) Patent No.: US 8,017,179 B2
(45) Date of Patent: Sep. 13, 2011

(54) COATINGS FOR IMPLANTABLE ELECTRODES

(75) Inventors: Liliana Atanasoska, Edina, MN (US); Ronald W. Heil, Roseville, MN (US); David M. Flynn, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 946 days.

(21) Appl. No.: 11/256,995

(22) Filed: Oct. 24, 2005

(65) Prior Publication Data

US 2006/0035026 A1 Feb. 16, 2006

Related U.S. Application Data

(62) Division of application No. 10/738,647, filed on Dec. 16, 2003.

(51) Int. Cl.
*B05D 5/12* (2006.01)
*B05D 3/02* (2006.01)

(52) U.S. Cl. ............ 427/126.3; 427/126.5; 427/2.1; 427/2.24; 427/58; 427/256

(58) Field of Classification Search .......... 427/327, 427/126.1, 126.5
See application file for complete search history.

(56) References Cited

U.S. PATENT DOCUMENTS

| | | | |
|---|---|---|---|
| 3,234,110 A | 2/1966 | Beer | |
| 4,003,817 A * | 1/1977 | Bianchi et al. | 204/290.03 |
| 4,126,934 A | 11/1978 | Richter et al. | |
| 4,156,429 A | 5/1979 | Amundson | |
| 4,587,975 A | 5/1986 | Salo et al. | |
| 4,677,989 A | 7/1987 | Robblee | |
| 4,717,581 A * | 1/1988 | Robblee | 427/2.12 |
| 4,762,136 A | 8/1988 | Baker, Jr. | |
| 4,797,182 A | 1/1989 | Beer et al. | |
| 4,919,135 A * | 4/1990 | Phillips et al. | 607/121 |
| 4,922,607 A | 5/1990 | Doan et al. | |
| 4,922,927 A | 5/1990 | Fine et al. | |
| 4,944,088 A | 7/1990 | Doan et al. | |
| 4,967,755 A | 11/1990 | Pohndorf | |
| 5,007,435 A | 4/1991 | Doan et al. | |
| 5,074,313 A | 12/1991 | Dahl et al. | |

(Continued)

FOREIGN PATENT DOCUMENTS

EP 0813885 6/1997

(Continued)

OTHER PUBLICATIONS

Robblee et al. Charge Injection Properties of Thermally-Prepared Iridium Oxide Films. Mat. Res. Soc. Symp. Proc. vol. 55. 1986, pp. 303-310.*

(Continued)

*Primary Examiner* — David Turocy
(74) *Attorney, Agent, or Firm* — Faegre & Benson LLP

(57) ABSTRACT

A method includes sandblasting an electrode surface, applying a conductive oxide precursor solution to the electrode surface, and heating the electrode for at least 5 minutes at a temperature between 350 degrees C. and 550 degrees C. to convert the precursor solution into an oxide coating. One method includes applying a composite material including a conductive component and a non-conductive component to an electrode and curing the composite material to form a coating on the electrode. One method includes providing a metallic oxide coating on an electrode surface and applying a galvanostatic treatment to the electrode to increase the effective surface area of the metallic oxide coating.

16 Claims, 7 Drawing Sheets

U.S. PATENT DOCUMENTS

| | | | |
|---|---|---|---|
| 5,143,090 A | | 9/1992 | Dutcher et al. |
| 5,156,726 A | | 10/1992 | Nakada et al. |
| 5,294,317 A | | 3/1994 | Saito et al. |
| 5,330,522 A | | 7/1994 | Kreyenhagen |
| 5,334,293 A | * | 8/1994 | Cairns et al. ............... 205/535 |
| 5,368,564 A | | 11/1994 | Savage |
| 5,405,373 A | * | 4/1995 | Petersson et al. ............ 607/121 |
| 5,464,404 A | | 11/1995 | Abela et al. |
| 5,476,502 A | | 12/1995 | Rubin |
| 5,507,725 A | | 4/1996 | Savage et al. |
| 5,534,022 A | | 7/1996 | Hoffmann et al. |
| 5,545,205 A | | 8/1996 | Schulte et al. |
| 5,632,770 A | | 5/1997 | Schaldach |
| 5,643,197 A | | 7/1997 | Brucker et al. |
| 5,645,580 A | | 7/1997 | Moaddeb et al. |
| 5,654,030 A | * | 8/1997 | Munshi et al. .............. 427/2.24 |
| 5,683,443 A | * | 11/1997 | Munshi et al. ............... 607/121 |
| RE35,924 E | | 10/1998 | Winkler |
| 5,824,016 A | | 10/1998 | Ekwall |
| 5,899,929 A | | 5/1999 | Thompson et al. |
| 5,920,126 A | | 7/1999 | Sohara |
| 5,935,102 A | | 8/1999 | Bowden et al. |
| 5,935,160 A | | 8/1999 | Auricchio et al. |
| 5,935,392 A | | 8/1999 | Lubin et al. |
| 5,954,649 A | | 9/1999 | Chia et al. |
| 6,006,134 A | | 12/1999 | Hill et al. |
| 6,029,091 A | | 2/2000 | de la Rama et al. |
| 6,263,250 B1 | | 7/2001 | Skinner |
| 6,295,474 B1 | | 9/2001 | Munshi |
| 6,516,232 B2 | | 2/2003 | Skinner |
| 6,677,557 B2 | | 1/2004 | Ito et al. |
| 7,421,299 B2 | * | 9/2008 | Frericks et al. ............... 607/116 |
| 2003/0215718 A1 | | 11/2003 | Huang et al. |
| 2005/0131509 A1 | | 6/2005 | Atanassoska et al. |

FOREIGN PATENT DOCUMENTS

| | | |
|---|---|---|
| EP | 0813886 | 12/1997 |
| GB | 2065478 | 7/1981 |
| WO | WO 01/84886 | 11/2001 |
| WO | WO-0184886 A1 | 11/2001 |

OTHER PUBLICATIONS

Blouin et al. Activation of Ruthenium Oxide, iridium Oxide, and Mixed RuxIr1-x Oxide Electrodes during Cathodic Polarization and Hydrogen Evolution. J. Electrochem. Soc., vol. 144, No. 2, Feb. 1997. pp. 573-581.*

Robblee, L. S., et al., "Activated IR: an electrode suitable for reversible change charge injection in saline solution", *Journal of the Electrochemical Society* 130(3), (1983),731-733.

"U.S. Appl. No. 09/352,557, Non Final Office Action mailed Sep. 29, 2000", 10 pgs.

"U.S. Appl. No. 09/352,557, Notice of Allowance mailed Mar. 1, 2001", 7 pgs.

"U.S. Appl. No. 09/352,557, Response filed Dec. 29, 2000 to Non Final Office Action mailed Sep. 29, 2000", 8 pgs.

"U.S. Appl. No. 09/907,540, Notice of Allowance mailed Sep. 30, 2002", 8 pgs.

"U.S. Appl. No. 10/738,647, Advisory Action mailed Nov. 20, 2008", 10 pgs.

"U.S. Appl. No. 10/738,647, Advisory Action mailed Sep. 25, 2006", 3 pgs.

"U.S. Appl. No. 10/738,647, Appeal Brief filed Feb. 17, 2009", 18 pgs.

"U.S. Appl. No. 10/738,647, Final Office Action mailed Aug. 15, 2008", 18 pgs.

"U.S. Appl. No. 10/738,647, Final Office Action mailed Jun. 5, 2007", 13 pgs.

"U.S. Appl. No. 10/738,647, Final Office Action mailed Jul. 19, 2006", 12 pgs.

"U.S. Appl. No. 10/738,647, Non Final Office Action mailed Nov. 21, 2005", 7 pgs.

"U.S. Appl. No. 10/738,647, Non Final Office Action mailed Dec. 27, 2006", 14 pgs.

"U.S. Appl. No. 10/738,647, Non-Final Office Action mailed May 14, 2009", 20 pgs.

"U.S. Appl. No. 10/738,647, Non-Final Office Action mailed Dec. 4, 2007", 16 pgs.

"U.S. Appl. No. 10/738,647, Pre-Appeal Brief Request mailed Dec. 15, 2008", 5 pgs.

"U.S. Appl. No. 10/738,647, Response filed Oct. 30, 2007 to Final Office Action mailed Jun. 5, 2007", 11 pgs.

"U.S. Appl. No. 10/738,647, Response filed Nov. 17, 2008 to Final Office Action mailed Aug. 15, 2008", 12 pgs.

"U.S. Appl. No. 10/738,647, Response filed Mar. 27, 2007 to Non Final Office Action mailed Dec. 27, 2006", 10 pgs.

"U.S. Appl. No. 10/738,647, Response filed May 19, 2006 to Non Final Office Action mailed Nov. 21, 2005", 9 pgs.

"U.S. Appl. No. 10/738,647, Response filed May 2, 2008 to Non-Final Office Action mailed Dec. 4, 2007", 13 pgs.

"U.S. Appl. No. 10/738,647, Response filed Jun. 13, 2005 to Restriction Requirement mailed May 12, 2005", 7 pgs.

"U.S. Appl. No. 10/738,647, Response filed Sep. 14, 2009 to Non Final Office Action mailed May 14, 2009", 16 pgs.

"U.S. Appl. No. 10/738,647, Response filed Sep. 19, 2006 to Final Office Action mailed Jul. 19, 2006", 10 pgs.

"U.S. Appl. No. 10/738,647, Response filed Sep. 23, 2005 to Restriction Requirement mailed Aug. 23, 2005", 5 pgs.

"U.S. Appl. No. 10/738,647, Restriction Requirement mailed May 12, 2005", 5 pgs.

"U.S. Appl. No. 10/738,647, Restriction Requirement mailed Aug. 23, 2005", 7 pgs.

U.S. Appl. No. 10/738,647, Final Rejection mailed Dec. 30, 2009, 23 pages.

U.S. Appl. No. 10/738,647, Response filed to Non-Compliant Amendment, dated Oct. 23, 2009, 16 pages.

U.S. Appl. No. 10/738,647, Notice of Non-Compliant Amendment mailed Oct. 21, 2009, 2 pages.

U.S. Appl. No. 10/738,647, Notice of Panel Decision from Pre-Appeal Brief Review, mailed Jan. 6, 2009, 2 pages.

U.S. Appl. No. 10/738,647, Notice of Appeal and Pre-Appeal Brief Request, mailed Dec. 15, 2008, 8 pages.

U.S. Appl. No. 10/738,647, Request for Continued Examination (RCE) filed Oct. 19, 2006.

Blouin et al., "Activation of Ruthenium Oxide, iridium Oxide, and Mixed RuxIr1-x Oxide Electrodes During Cathodic Polarization and Hydrogen Evolution", J. Electrochem. Soc., vol. 144, No. 2, Feb. 1997, pp. 573-581.

Robblee, L.S. et al., "Charge Injection properties of Thermally-Prepared Iridium Oxide Films", Mat. Res. Soc. Symp. Proc. vol. 55, 1986, pp. 303-310.

Final Office Action issued in U.S. Appl. No. 10/738,647, mailed Oct. 25, 2010.

* cited by examiner

COATINGS FOR IMPLANTABLE ELECTRODES

CROSS-REFERENCE TO RELATED APPLICATION(S)

This application is a division of U.S. patent application Ser. No. 10/738,647, filed on Dec. 16, 2003, the specification of which is incorporated herein by reference.

TECHNICAL FIELD

This invention relates to the field of medical leads, and more specifically to a coating for an electrode.

BACKGROUND

Leads having electrodes implanted in or about the heart have been used to reverse certain life threatening arrhythmia, or to stimulate contraction of the heart. Electrical energy is applied to the heart via an electrode to return the heart to normal rhythm. Leads are usually positioned on or in the ventricle or the atrium and the lead terminal pins are attached to a pacemaker or defibrillator which is implanted subcutaneously.

Some factors that affect electrode performance include polarization at the electrode/tissue interface, electrode capacitance, sensing impedance, and voltage threshold. What is needed is electrodes that are constructed to optimize these factors as needed.

SUMMARY

A method comprising sandblasting an electrode surface, applying a conductive oxide precursor solution to the electrode surface, and heating the electrode for at least 5 minutes at a temperature between 350 degrees C. and 550 degrees C. to convert the precursor solution into an oxide coating.

One aspect includes applying a composite material including a conductive component and a non-conductive component to an electrode and curing the composite material to form a coating on the electrode.

One aspect includes providing a metallic oxide coating on an electrode surface and applying a galvanostatic treatment to the electrode to increase the effective surface area of the metallic oxide coating.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

A conductive oxide coating, such as an iridium oxide coating, on an electrode for an implantable lead is described herein. In various embodiments, the electrode can be one or more of the electrodes shown in FIGS. 1-4.

Figure 1:
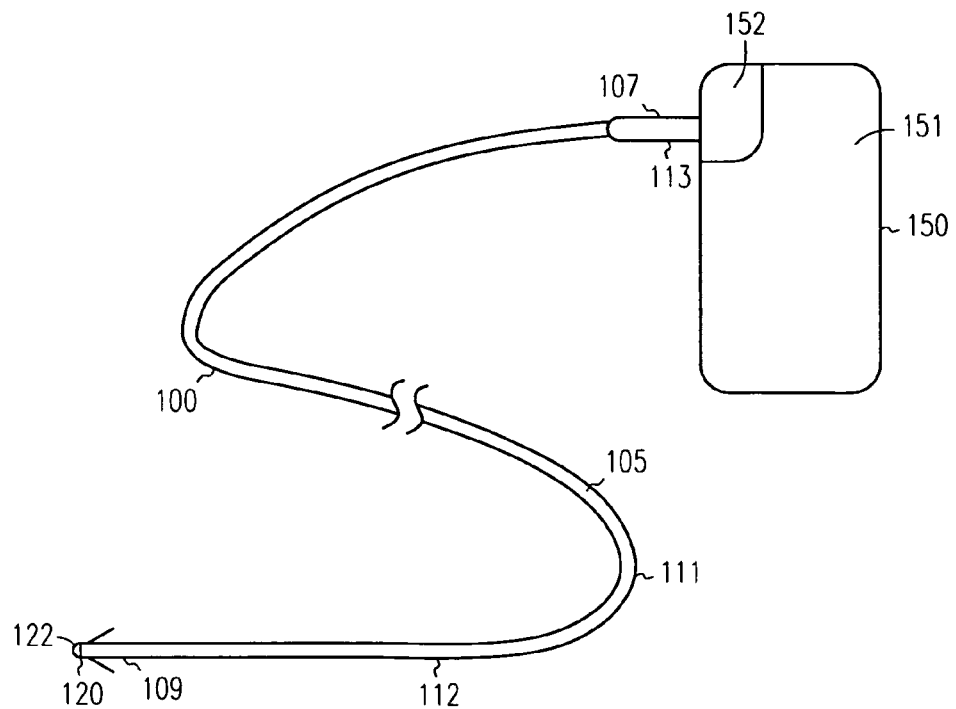
FIG. 1 shows a lead and pulse generator in accordance with one embodiment.

FIG. 1 shows a view of a lead 100 coupled to a pulse generator 150. In one embodiment, lead 100 is adapted to deliver pacing energy to a heart. Some examples deliver defibrillation shocks to a heart. Pulse generator 150 can be implanted in a surgically-formed pocket in a patient's chest or other desired location. Pulse generator 150 generally includes electronic components to perform signal analysis, processing, and control. Pulse generator 150 can include a power supply such as a battery, a capacitor, and other components housed in a case or can 151. The device can include microprocessors to provide processing and evaluation to determine and deliver electrical shocks and pulses of different energy levels and timing for ventricular defibrillation, cardioversion, and pacing to a heart in response to cardiac arrhythmia including fibrillation, tachycardia, and bradycardia.

In one embodiment, lead 100 includes a lead body 105 extending from a proximal end 107 to a distal end 109 and having an intermediate portion 111. Lead 100 includes one or more conductors, such as coiled conductors or other conductors, to conduct energy from pulse generator 150 to an electrode 120, and also to receive signals from the heart. The lead further includes outer insulation 112 to insulate the conductor. The conductors are coupled to one or more electrodes, such as electrode 120. Lead terminal pins 113 are attached to pulse generator 150 at a header 152. The system can include a unipolar system with the case acting as an electrode or a bipolar system with a pulse between two distally located electrodes.

In one embodiment, electrode 120 includes an electrode body formed of platinum iridium (PtIr) and an outer surface having at least a portion of the outer surface coated by a conductive oxide coating 122, such as an iridium oxide (IrOx) coating. In some examples, pulse generator can 151 can be used as an electrode and include an oxide coating as disclosed herein. In some examples, a header electrode can be placed in or near the header 152 of can 151.

Figure 2:
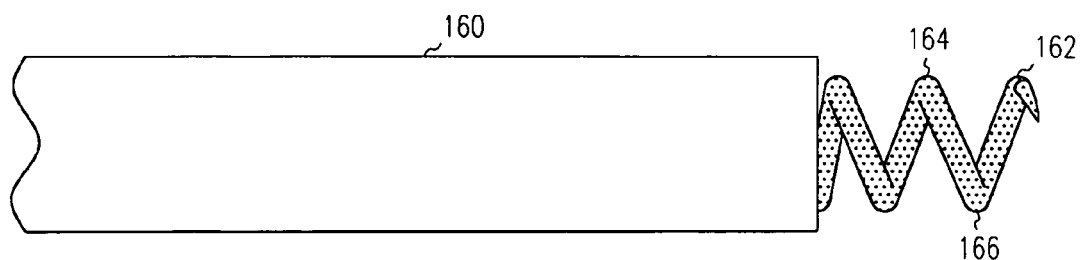
FIG. 2 shows a helix electrode in accordance with one embodiment.

FIG. 2 shows an example of a lead 160 having a helix 162. In one embodiment, helix 162 can be electrically active and can be used to screw into the myocardium to actively fixate the electrode to the heart. Helix 162 includes an outer surface 164 at least partially having a conductive oxide coating 166, such as an IrOx coating on the surface of the helix.

Figure 3:
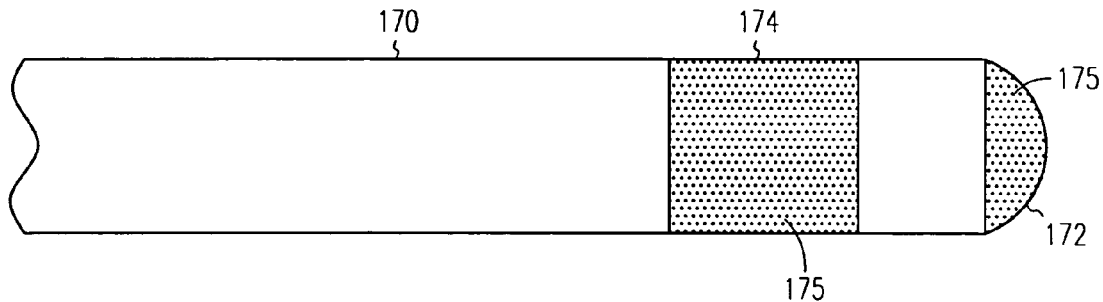
FIG. 3 shows a bipolar lead in accordance with one embodiment.

FIG. 3 shows a bipolar lead 170 having a tip electrode 172 and a ring electrode 174 located on the intermediate portion of the lead proximally from the tip electrode 172. Either one or both of the electrodes 172 and 174 can have a conductive oxide coating 175 thereon.

Figure 4:
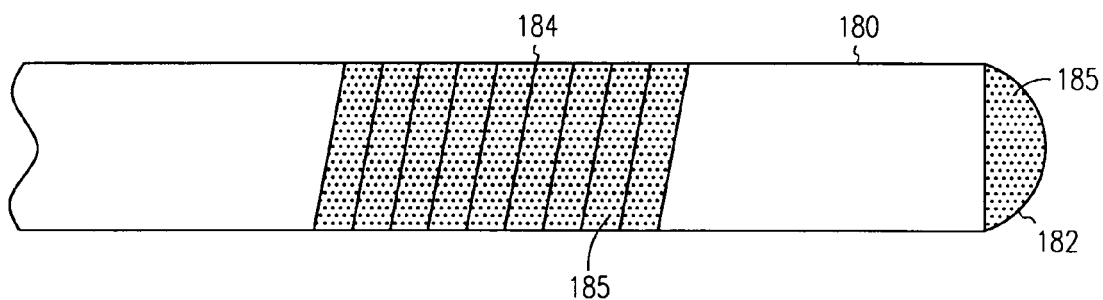
FIG. 4 shows a defibrillation coil electrode in accordance with one embodiment.

FIG. 4 shows a defibrillation lead 180 having a pacing/sensing tip electrode 182 and a defibrillation coil electrode 184. Either or both electrodes 182 and 184 can have a conductive oxide coating 185 thereon.

One embodiment of the present system provides a process for thermal decomposition of a conductive oxide coating, such as an IrOx coating, on a PtIr electrode. The present process allows IrOx (or another coating material) to adhere well to PtIr electrodes (and other base materials). When compared to current electrodes, IrOx coated PtIr electrodes have lower polarization, higher capacitance, lower sensing impedance, and lower voltage thresholds.

Lower polarization is desired since, during pacing, charge builds up at the electrode/tissue interface. This charge build up is called polarization. As the magnitude of this charge increases, more energy is required to capture the heart. In one embodiment, applying the IrOx coating to PtIr electrodes can lower the polarization to about ⅓ of its initial value, as measured by the galvanic square wave (GSW) method.

Electrode capacitance is directly proportional to charge storage capacity ($mC/cm^2$). Applying the IrOx coating to PtIr electrodes by one embodiment of the present thermal decomposition process can increase its capacitance by 30 to 40 times when measured by cyclic voltammetry (CV) or electrochemical impedance spectroscopy (EIS). The IrOx coating significantly increases the electrode charge storage capacity and allows for safe deliveries of charge densities that are much greater than those achieved with uncoated PtIr electrodes.

Sensing impedance is inversely proportional to electrode surface area. Smaller electrodes are being developed as a result of diminishing lead body size and in an effort to increase pacing impedance. Therefore, the sensing impedance is rising because the electrode surface area is dropping. If the sensing impedance in a lead is too high, an autocapture feature of the pulse generator will not work, for example. Autocapture is a technology that verifies if a pacing pulse delivered to the heart for purposes of pacing has actually paced the heart. The autocapture algorithm looks at electrical activity generated by the heart (evoked response) after the pacing pulse has been delivered. A high capacitance coating will tend to reduce the charge introduced by the pacing pulse, thus resulting in improved sensing properties needed for autocapture. The IrOx coating is very porous. This coating will dramatically increase the effective surface area of the electrode with a minimal increase in volume. Applying the IrOx coating to standard PtIr electrodes can lower the sensing impedance by 70%.

In the past, the voltage thresholds associated with smooth electrodes were relatively high because of the thickness of the scar tissue layer between the electrode and the live tissue. One of the factors that contributes to the thickness of the scar tissue is the relative motion between the electrode and the tissue. Some pacing electrodes include a mesh screen. Leads manufactured with this type of electrode had lower voltage thresholds because this design helped to promote tissue ingrowth into the electrode and therefore minimized the amount of scar tissue that developed. The IrOx coating can be applied to almost any electrode. The cavities in the IrOx surface are approximately the same size as the heart tissue cells and therefore this type of coating should promote better tissue ingrowth than the mesh screen electrodes. As a result, the voltage thresholds associated with the IrOx coated electrodes can be lower.

High surface area coatings, such as the IrOx coating described herein, may lower voltage thresholds to a point where steroid technology may not be needed. Moreover, the coating will remain a constant feature of the electrode. In contrast, steroid eluting leads leave open the possibility of the drug eventually being released in subtherapeutic levels or even running out. IrOx coating will thereby simplify lead designs, subsequently lowering manufacturing costs and producing a more reliable lead for the patient. The IrOx coating described herein will improve sensing features of the pulse generators, for example, one key improvement being that of autocapture. Further, this process provides a means to produce chronically stable electrode coatings upon inert noble metal electrode substrates.

Figure 5:
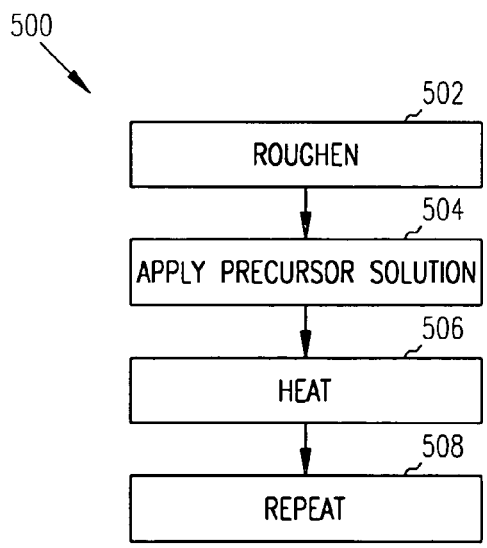
FIG. 5 shows a method of coating an electrode in accordance with one embodiment.

FIG. 5 shows a method 500 for forming an iridium oxide coating on an electrode, in accordance with one embodiment. Method 500 includes roughening the electrode surface (502), applying a precursor solution to the electrode (504), and heating the electrode to form the iridium oxide coating (506). The applying and heating steps are repeated as desired (508).

In one example, roughening can include sandblasting a platinum iridium electrode surface. The sandblasting is accomplished using a sandblasting media of appropriate chemical composition and particle size prior to application of the precursor solution. For example, it can include sandblasting the electrode surface with 50 μm size SiC for 5 minutes or more. One embodiment includes sandblasting the electrode surface with 10 μm size $Al_2O_3$. One embodiment utilizes 50 μm $SiO_2$. In some embodiments, after sandblasting the electrode, the electrode can be placed in an oxalic acid (10%) for about 30 minutes.

In one example, applying a conductive oxide precursor solution to the electrode surface can include coating or soaking the electrode in the solution. In some embodiments, the precursor solution includes an iridium precursor solution. Other embodiments use other transition metals, such as ruthenium, rhodium, or osmium, for example. In one embodiment, the iridium precursor solution can include a 0.05 moles/liter to 0.3 moles/liter solution of iridium ($Ir^{+3}$ or $Ir^{+6}$) in isopropanol or other alcohol, or a mixture of alcohol and water. In one embodiment, the precursor solution includes a 0.1 to 0.2 moles/liter solution of iridium in an alcohol. In other embodiments, the precursor solution can be applied by dipping, brushing, or spraying the precursor solution onto the surface of the electrode.

The electrode is then heated to convert the metal precursor into a metal oxide. In one example, heating the electrode can include heating the electrode for at least 5 minutes at a temperature between 350 degrees C. and 550 degrees C. to convert the precursor solution into iridium oxide. Some embodiments heat the electrode for between about 5 to about 25 minutes. In one embodiment, the heating is in the range of 350 degrees C. to 450 degrees C. This range provides an optimally low polarization, high capacitance coating, as will be further discussed below. In one embodiment, the heating is in the range of 500 degrees C. to 550 degrees C., to provide a high corrosion resistant electrode.

In one embodiment, the precursor solution is applied and the electrode is heated at least 4 times and then a final annealing is done at the same temperature as the firing. In one option, the annealing can be done for 1 to 2 hours. Some embodiments apply 2 applications to 12 applications of oxide on the electrode. One embodiment applies 5 applications of oxide coating.

The present thermal decomposition coating technique can be done on a pacing electrode, tip electrode, a ring electrode, a defibrillation coil electrode, a header electrode, or a pulse generator can. In various examples, the process can be used on electrodes for leads designed to treat bradyarrhythmias, tachyarrhythmias, atrial flutter, atrial fibrillation, or congestive heart failure, for example.

In one embodiment, the process is optimized to provide low polarization for a PtIr electrode. For example, the method can include applying a 0.05 molars/liter to 0.3 molars/liter iridium precursor solution to a PtIr electrode surface, heating the electrode for at least 5 minutes at a temperature between 350 degrees C. and 450 degrees C. to convert the precursor solution into iridium oxide, repeating the applying and heating steps at least three times, and annealing the electrode for at least 1 hour at 350 to 450 degrees C. after the last coat of precursor solution has been applied. This process provided a IrOx coating of approximately 2 microns or greater.

The process outlined above optimizes the electrode surface to provide high capacitance and low polarization. A heating range between 350 degrees C. to 450 degrees C. for 5 to 25 minutes and a final annealing at the same temperature for about 1 to 2 hours produces a high capacitance, low polarization coating. The coating has a distinctive mud cracked structure having a capacitance of 50 $mF/cm^2$ or greater in phosphate buffered saline or Hanks solution. The capacitance value being derived from cyclic voltrammy measurements. The present process provides a more uniform mud-cracked structure with an increased electrochemically active surface area than past electrodes.

Figure 6:
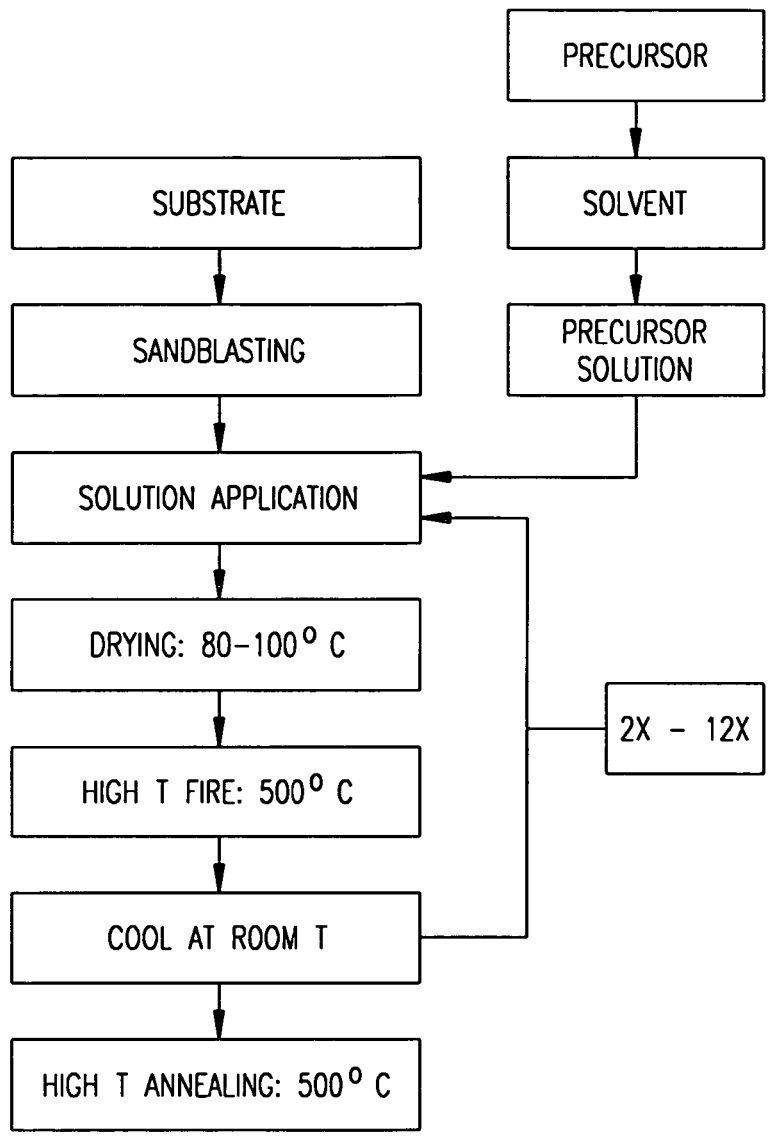
FIG. 6 shows a method of coating an electrode in accordance with one embodiment.

FIG. 6 shows a method of coating an electrode with a conductive oxide, in accordance with one embodiment. The method of FIG. 6 optimizes corrosion resistance. The method includes sandblasting the electrode surface, applying a precursor solution of a conductive oxide to the electrode. For example, an iridium precursor solution of 0.05 to 0.5 moles/liter can be used. One embodiment utilizes a precursor solution of 0.1 to 0.2 moles/liter. The coated electrode is dried at 80-100 degrees C. for about 10 minutes. The coated electrode is then fired at between 500-550 degrees C. for 5 to 25 minutes. In various embodiments, 2 to 12 applications are put on, resulting in coating which is about 2 microns thick or greater. There is a final annealing step at 500 to 550 degrees C. for 1 to 2 hours.

This method produces a highly corrosion resistance coating with a low anodic dissolution rate even at a high current density of about 0.5 $A/cm^2$. This process provides an electrode having a capacitance of 10 $mF/cm^2$ in phosphate buffered saline or Hanks solution, as derived from cyclic voltramemetry and electrochemical impedance spectroscopy measurement.

In one example, the process of FIG. 6 can be applicable to a bipolar lead with a ring electrode having the high corrosion coating and the tip electrode having the low polarization process discussed above. In one example, the high corrosion resistance process can be used on a heart failure lead having one or more electrodes adapted to be placed in the coronary sinus and designed to deliver between 7.5 V and 10 V. The tip and/or ring electrodes of such an example can utilize the high corrosion resistance examples.

High corrosion resistance is needed because when the amount of energy transferred through the surface of an electrode into tissue exceeds a certain critical value, the electrode begins to breakdown or corrode. In the past, electrode corrosion was not an issue because voltage thresholds were relatively low and electrode surface areas were large. As the size of electrodes decrease, corrosion becomes a problem. The rough and irregular surface of the IrOx coating increases the effective surface area of the pacing electrode considerably with a minimum change in electrode size. Moreover, applying the corrosion resistant IrOx coating to PtIr electrodes also can lower polarization up to ⅓ of its initial value, as measured by galvanic square wave (GSW) method.

The present corrosion resistant method can also increase capacitance 5 to 10 times when measured using cyclic voltammatry or electrochemical impedance spectroscopy, and it can also lower sensing impedance by up to 70%. Moreover, the cavities in the IrOx surface are approximately the same size as the heart tissue cells and therefore this type of coating should promote better tissue ingrowth than mesh screen electrodes. As a result, the voltage thresholds associated with IrOx coated electrodes is lower.

Figure 7:
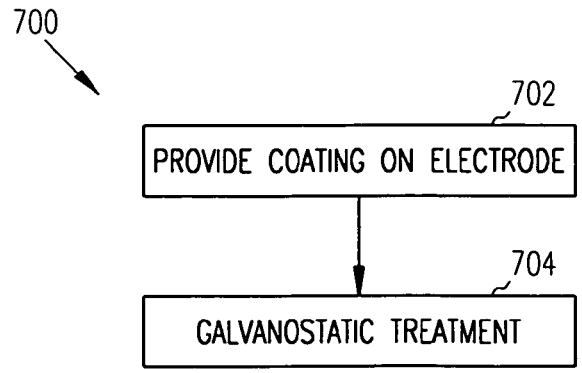
FIG. 7 shows a method of galvanostatic treatment of a coated electrode, in accordance with one embodiment.

FIG. 7 shows a method 700 according to one embodiment. Method 700 provides a galvanostatic process for electrodes allowing the electrode coating to be tuned to the desired performance. A galvanostatic process includes a process of subjecting an electrode to either a positive or negative constant current for a specified time duration. This process can be used to significantly increase the effective macro and microscopic surface area of electrodes coated with IrOx, for example. Increasing the effective surface area of an electrode enhances its charge injection efficiency and reduces polarization losses at the electrode/tissue interface.

In one embodiment, method 700 includes providing a conductive oxide coating, such as an iridium oxide coating, on an electrode surface (702), and applying a galvanostatic treatment to the electrode to increase the effective surface area of the iridium oxide coating (704).

In one embodiment, the process can include subjecting an IrOx coating to the galvanostatic treatment at constant current density for the time duration required to produce a coating morphology with the desired charge injection efficiency (optimized charge injection efficiency). The constant current density used for one example is 8.5 mA/cm2 for a duration of 30 minutes. In another example, the electrode including the coating is subjected to a galvanostatic treatment for at least 30 minutes. In some examples, a square wave or a sinusoidal waveform of between about 30 Hz to 120 Hz and 1 to 10 volts is used to apply the galvanostatic treatment to the electrode. The electrode can be placed in a solution such as sulfuric acid, for example, and subjected to the constant current galvanostatic treatment. The sulfuric acid bath concentration can range from 0.1 to 10 N. This process can be used to reduce polarization losses and increase the capacitance of the electrode. In some embodiments, the process can utilize square wave or sine wave fields to modify and optimize the coating as desired so as to increase surface area and lower the polarization of the electrode.

Table 1 shows the results before and after a galvanostatic treatment performed according to one embodiment. The polarization behavior of the IrOx coating before and after the galvanostatic treatment was measured in Hanks solution by using a GSW method set at 2.5 mA, 5 ms constant current square wave (see also FIG. 8), and a GSW method set at 2.5 mA, 10 ms constant current square wave (see also FIG. 9). The increase in the electrochemically active surface area was measured by cyclic voltammetry at a 50 mV/s scan rate.

TABLE 1

| | Sample | | | |
|---|---|---|---|---|
| | dV/dt, V/s GSW at 2.5 mA, 5 ms | dV/dt, V/s GSW at 2.5 mA, 10 ms | Charge Q, mC | Capacitance C, mF/cm$^2$ |
| Before | 24.9 | 16.05 | 0.53 | 8.98 |
| After | 6.5 | 5.45 | 1.588 | 26.915 |

Figure 8:
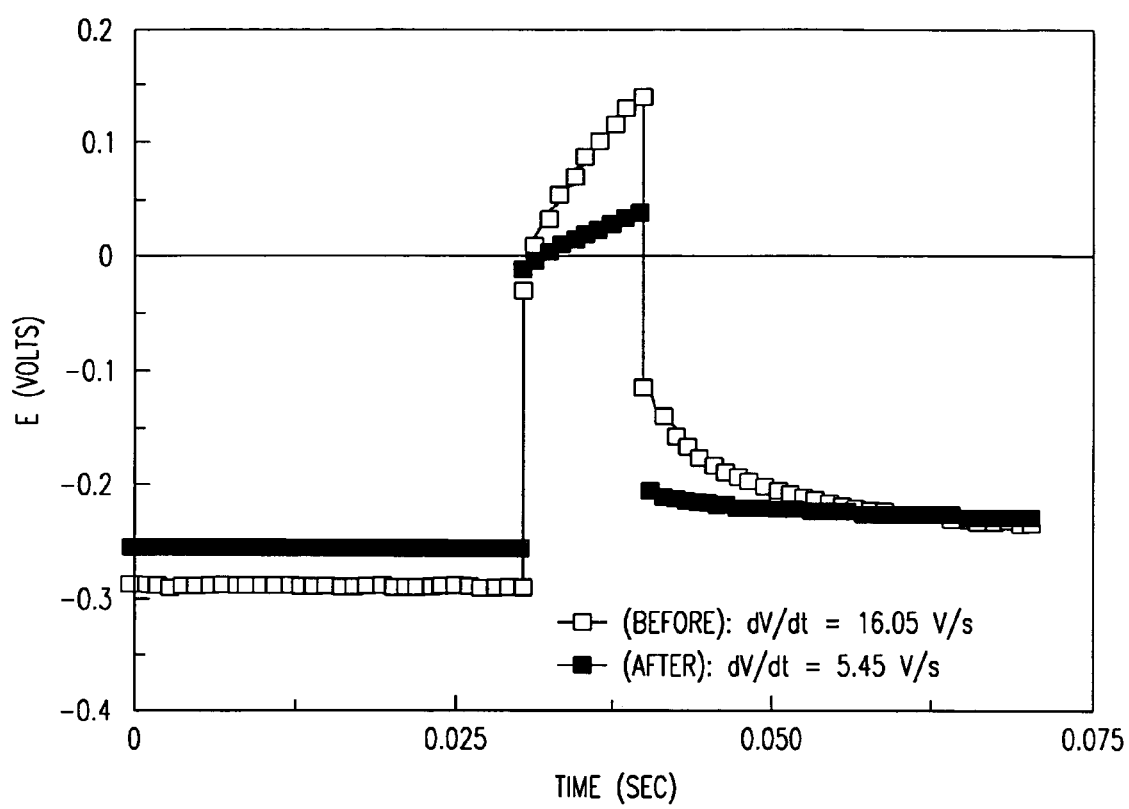
FIG. 8 shows test results of an electrode before and after a galvanostatic treatment in accordance with one embodiment.
Figure 9:
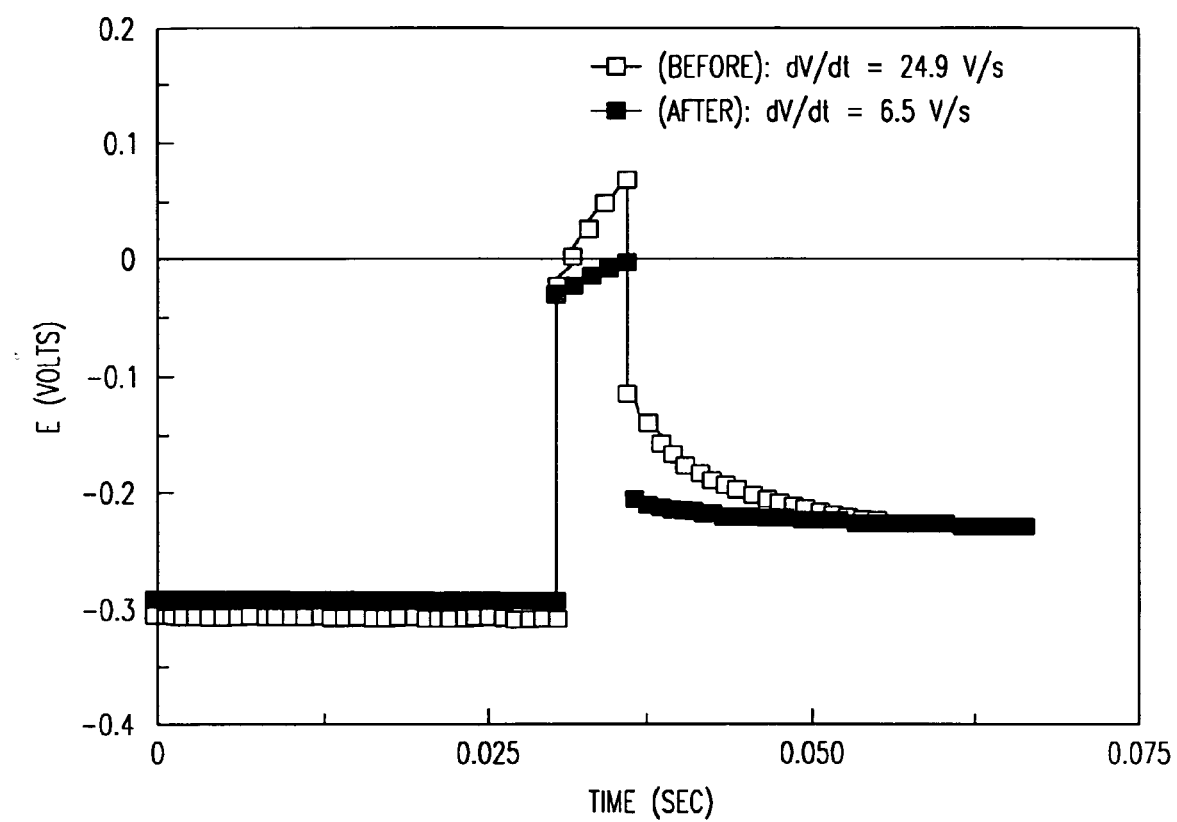
FIG. 9 shows test results of an electrode before and after a galvanostatic treatment in accordance with one embodiment.
Figure 10:
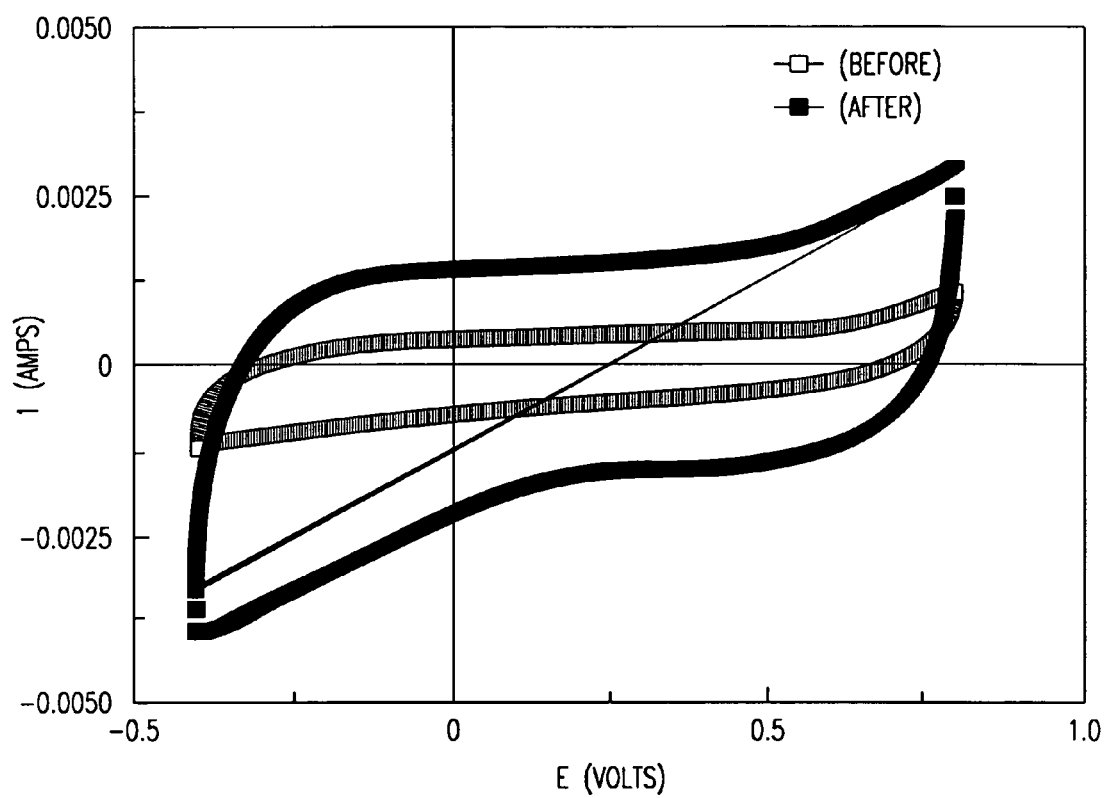
FIG. 10 shows test results of an electrode before and after a galvanostatic treatment in accordance with one embodiment.

FIGS. 8-10 show graphic results of sample electrodes before and after galvanostatic treatment. The galvanostatic treatment of the electrodes of FIGS. 8-10 was a positive constant current treatment at 10 mA for a duration of 30 minutes. The current density was 8.5 mA/cm$^2$. In FIG. 10, the before and after graphs were measured by a cyclic voltammetry method set at a 50 m/s scan rate. FIGS. 8 and 9 show how after the present treatment, electrodes have reduced polarization losses. FIG. 10 shows that the charge efficiency of the electrodes increases after the treatment.

The galvanostatic process enhances the performance of electrodes coated by IrOx, or other conductive oxides, by any method, including, but not limited to, the methods disclosed above. In general, the process provides a technique to further tailor or control the surface are to achieve targeted electrochemical performance, e.g., capacitance. It further allows a batch process electrode to be tailored or enhanced for specific properties. In other embodiments, this process can be used on any lead or electrode. For example, it can be used on a RuOx electrode. It can also be used on capacitors and supercapacitors. For example, an anode or cathode foil used in a stacked or rolled capacitor could have a coating and/or a galvanostatic treatment as described above to increase the surface area (and hence the capacitance) of the capacitor.

Figure 11:
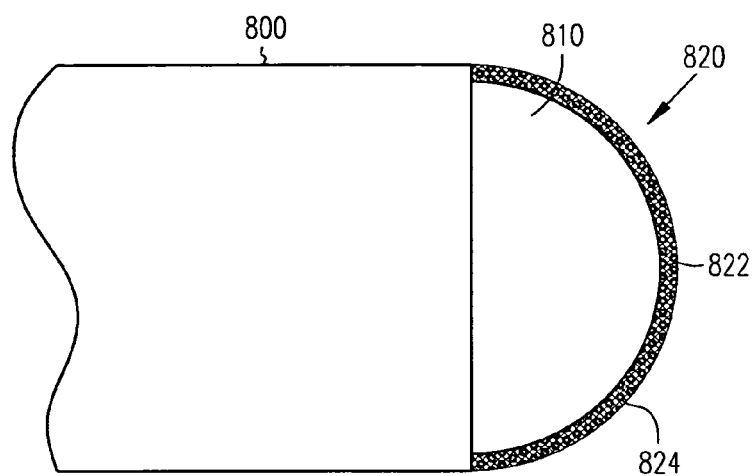
FIG. 11 shows an electrode having a composite coating in accordance with one embodiment.
Figure 12:
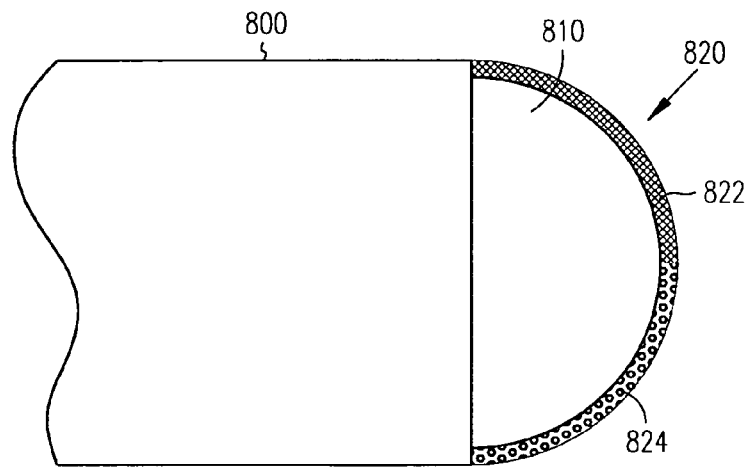
FIG. 12 shows an electrode having a composite coating in accordance with one embodiment.
Figure 13:
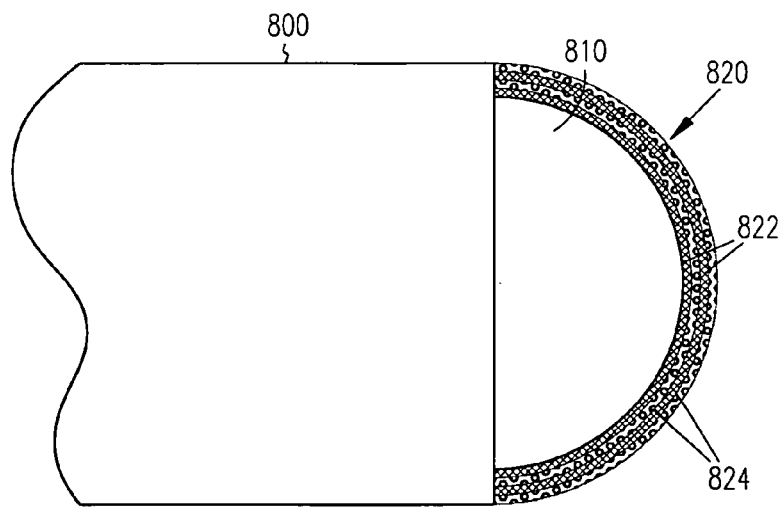
FIG. 13 shows an electrode having a composite coating in accordance with one embodiment.

FIGS. 11-13 show cross-sections of electrodes having coatings according to one or more embodiments. The coatings in the Figures are not shown to scale but are larger for sake of clarity.

FIG. 11 shows an electrode 800 according to one embodiment. Electrode 800 includes an electrode body 810, which can be PtIr or other material. In this example, a composite coating 820 is applied over at least a portion of the electrode surface. Composite coating 820 can include a conductive component 822, such as IrOx, and a non-conductive component 824, such as TaOx. In various embodiments, the conductive component is 5% to 95% of the composite material. In one example, the conductive component is 5% to 100% of the composite material. In one embodiment, the conductive component 822 is dispersed uniformly throughout the composite coating.

Conductive component 822 is chosen to have good polarization characteristics (low polarization), and can include materials such as IrOx, RuOx, RhOx, OsOx, or other transition metal. The non-conductive component 824 provides a material having high impedance, good mechanical properties, and the ability to disperse the conducting material in a desired fashion. For pacing, good catalytic properties of the conducting oxide component translate into low polarization resistance. In addition, the quantity of the non-conducting component can be varied to control the pacing impedance. This process produces electrodes that use less energy while still preserving the polarization characteristics of the conducting pseudo-capacitive oxide.

When designing electrodes for leads, one approach to extend the device battery life is to develop high pacing impedance electrodes. The present process provides a composite coating which can be tailored to have specific impedance properties. In one embodiment, the electrodes are coated with the composite material using a thermal deposition process, such as described above. The pacing impedance can be controlled by varying the amounts of IrOx and TaOx in the mixture. Electrodes having pacing impedances from approximately 500 Ohms (100% IrOx) to 700 Ohms (50% IrOx, 50% TaOx) can be produced using the process, for example. In one example, the process can produce electrodes with pacing impedances of about 880 Ohms.

In some embodiments, it is possible to vary the pacing impedance across the length of the electrode (a low impedance distal end/high impedance proximal end on a helix, for example). The present technique allows a manufacturer to control the pacing impedance of the electrode, thus making the manufacture of high pacing impedance electrodes easier and more precise. Moreover, electrodes coated with the mixture will be less susceptible to micro-dislodgement because the roughened surface characteristics of both IrOx and TaOx coating promote tissue ingrowth.

FIG. 12 shows an example where the conductive coating 822 is applied non-uniformly to electrode 800. In this example, there is a discrete interface between conductive component 822 and non-conductive component 824.

FIG. 13 shows another example where the conductive coating 822 is applied non-uniformly to electrode 800. In this example, one or more alternating layers of conductive component 822 and non-conductive component 824 are applied to the electrode surface.

In various embodiments, the composite coating described above can be applied to electrodes including a helix, a tip electrode, a ring electrode, and a defibrillation coil electrode.

In one embodiment, a method of applying the composite coating can include roughening the electrode surface, applying a composite material to the electrode, the composite material having a conductive component and a non-conductive component, and heating the electrode to turn the composite material into a coating on the electrode. The conductive component can include an IrOx precursor solution and the non-conductive component can include a TaOx precursor solution. In one example, the mixture comprises an $IrO_2$—$Ta_2O_5$ combination coated on a PtIr base metal electrode surface or other suitable metal or ally substrate. In one embodiment, the conductive component includes a RuOx precursor solution. Other examples utilize other transition metals as discussed above. In one example, the electrode is heated from 350 degrees C. to 550 degrees C. for between 5 minutes and 30 minutes and coated as often as needed and then having a final annealing of 1 to 2 hours.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A method comprising:
providing an implantable electrode configured for use with an implantable lead, the electrode having an electrode surface;
roughening the electrode surface;
applying a composite coating material to the electrode surface, the composite coating material having a conductive component comprising a transition metal oxide precursor solution and a non-conductive component, wherein the conductive component comprising the transition metal oxide precursor solution and the non-conductive component are applied non-uniformly to the electrode surface to form a composite coating having a discrete interface between the conductive component and the non-conductive component;

heating the electrode to turn the composite coating material into the composite coating having a conductive component comprising a transition metal oxide and a non-conductive component on the electrode surface; and after heating, increasing a charge injection efficiency of the transition metal oxide in the conductive component of the composite coating by subjecting the implantable electrode to a galvanostatic treatment including applying a constant current to the electrode in a solution.

2. The method of claim 1, wherein the conductive component includes an iridium oxide precursor solution.

3. The method of claim 1, wherein the non-conductive component includes a tantalum oxide precursor solution.

4. The method of claim 1, wherein the electrode is heated from 350 degrees C. to 550 degrees C. for at least 5 minutes.

5. The method of claim 4, wherein the electrode is heated for less than about 30 minutes.

6. The method of claim 1, wherein the conductive component includes a ruthenium oxide precursor solution.

7. The method of claim 1, wherein the composite material includes between 5% and 95% of the conductive component.

8. A method comprising:

applying a composite material including a conductive component comprising a transition metal oxide precursor solution and a non-conductive component to a PtIr substrate electrode having an electrode surface, wherein the conductive component and the non-conductive component are applied non-uniformly to the electrode surface to provide a discrete interface between the conductive component and the non-conductive component;

curing the composite material to form a coating including a conductive component comprising a transition metal oxide and a non-conductive component on the electrode surface; and after curing, increasing a charge injection efficiency of the transition metal oxide in the composite coating by subjecting the electrode to a galvanostatic treatment including applying a constant current to the electrode in a solution.

9. The method of claim 8, wherein the conductive component comprises iridium oxide and the non-conductive component comprises tantalum oxide.

10. The method of claim 8, wherein the conductive component comprises iridium oxide.

11. The method of claim 8, wherein the conductive component includes one or more of iridium oxide, ruthenium oxide, rhodium oxide, and osmium oxide.

12. The method of claim 8, wherein the composite material includes between 5% and 95% of the conductive component.

13. The method of claim 8, wherein curing the composite material includes heating the composite material at a temperature between 350 degrees C. to 550 degrees C. for at least 5 minutes.

14. A method comprising:

providing an implantable PtIr electrode configured for use with an implantable lead, the electrode having an electrode surface;

roughening the electrode surface;

applying a composite material to the electrode surface, the composite material having a conductive component comprising a transition metal oxide precursor solution and a non-conductive component wherein the conductive component and the non-conductive component are applied non-uniformly to the electrode surface to provide a discrete interface between the conductive component and the non-conductive component;

heating the electrode to convert the composite material into a coating on the electrode, the coating having a conductive component comprising a transition metal oxide and a non-conductive component; and after heating, increasing a charge injection efficiency of the transition metal oxide in the coating by subjecting the implantable electrode to a galvanostatic treatment including applying a constant current to the electrode in a solution for at least 30 minutes.

15. The method of claim 14, wherein the coating comprises iridium oxide and tantalum oxide.

16. The method of claim 14, wherein heating the electrode includes heating the composite material at a temperature between 350 degrees C. to 550 degrees C. for at least 5 minutes.

* * * * *